United States Patent [19]
Trowbridge et al.

[11] Patent Number: 5,648,469
[45] Date of Patent: Jul. 15, 1997

[54] MONOCLONAL ANTIBODIES REACTIVE WITH TRANSFERRIN RECEPTOR CYTOPLASMIC DOMAIN

[75] Inventors: Ian S. Trowbridge, San Diego; Suhaila N. White, Poway, both of Calif.

[73] Assignee: The Salk Institute for Biological Studies, La Jolla, Calif.

[21] Appl. No.: 444,418

[22] Filed: May 19, 1995

Related U.S. Application Data

[63] Continuation of Ser. No. 871,105, Apr. 20, 1992, abandoned.
[51] Int. Cl.$^6$ .................. C07K 16/28; C07K 14/705; C12N 5/20
[52] U.S. Cl. .................. 530/388.22; 530/388.8; 530/388.85; 530/394; 435/70.21; 435/172.2; 435/334
[58] Field of Search ............ 435/70.21, 240.27, 435/172.2; 530/388.2, 388.22, 388.75, 388.85, 388.9; 935/95, 89, 104

[56] References Cited

U.S. PATENT DOCUMENTS 4,626,507  12/1986  Trowbridge et al. .................. 435/240

OTHER PUBLICATIONS

Waldman (1991) Science 252:1657–1662.
Harlow et al. (1988) "Antibodies: A Laboratory Manual", Cold Spring Harbor Press, Cold Spring Harbor, N.Y. pp. 72–77, 92–97, 128–135 & 141–157.
Jing et al (1990) J. Cell Biol. 110:283–294.
McClelland et al. (1984) Cell 39: 267–274.
Trowbridge et al (1992) J. Inorganic Biochem. 47: 209–217.
Collawn et al. (1990) Cell 63: 1061–1072.
Schneider et al. (1984) Nature 311: 675–678.
Alvarez et al. (1990) Biochem. J. 267: 31–35.
Trowbridge et al (1982) Proc. Nat'l Acad Sci. 79: 1175–1179.
White et al (1992) Biochim. Biophys. Acta. 1136: 28–34.
Rutledge et al (1991) J. Biol. Chem. 266(31): 21125–21130.
Yoshimori et al (1988) Cell Structure & Function 13: 311–324.
Trowbridge et al (1981) Proc. Nat'l Acad. Sci. 78(5): 3039–3043.
Roitt (1991) "Essential Immunology", Blackwell Scientific Publications, London, pp. 65–66.
Harris et al (1993) Trends in Biotechnol. 11: 42–44.
Gregoriadis et al (1993) Trends in Biotechnol. 11: 440–442.

*Primary Examiner*—Donald E. Adams
*Assistant Examiner*—Jacqueline G. Krikorian
*Attorney, Agent, or Firm*—Fish and Richardson P.C.

[57] ABSTRACT

Monoclonal antibodies have been produced which specifically bind to epitopes found in the cytoplasmic domain of the transferrin receptor (TR). The antibodies are useful for isolating sequences in a sample which contain TR cytoplasmic domain.

5 Claims, 1 Drawing Sheet

MEMBRANE

```
            MAb    MAb    MAb                           61
            H68.4  H73.2  I60.1
Human    1  MMDQARSAFSNLFGGEPLSYTRFSLARQVDGDNSHVEMKLAVDEEENADNNTKANVTKPKR
Mouse                                    A           M   S  R
Hamster                    C
```

FIGURE 1

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..7

( x i ) SEQUENCE DESCRIPTION: SEQ ID NO:1:

```
Val  Asp  Gly  Asp  Asn  Ser  His
 1                    5
```

( 2 ) INFORMATION FOR SEQ ID NO:2:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: human ( i x ) FEATURE:
        ( A ) NAME/KEY: Protein
        ( B ) LOCATION: 1..61

( x i ) SEQUENCE DESCRIPTION: SEQ ID NO:2:

```
Met  Met  Asp  Gln  Ala  Arg  Ser  Ala  Phe  Ser  Asn  Leu  Phe  Gly  Gly  Glu
 1                    5                   10                     15

Pro  Leu  Ser  Tyr  Thr  Arg  Phe  Ser  Leu  Ala  Arg  Gln  Val  Asp  Gly  Asp
                20                   25                     30

Asn  Ser  His  Val  Glu  Met  Lys  Leu  Ala  Val  Asp  Glu  Glu  Glu  Asn  Ala
                35                   40                     45

Asp  Asn  Asn  Thr  Lys  Ala  Asn  Val  Thr  Lys  Pro  Lys  Arg
        50                   55                     60
```

( 2 ) INFORMATION FOR SEQ ID NO:3:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Mouse ( i x ) FEATURE:
        ( A ) NAME/KEY: Protein
        ( B ) LOCATION: 1..61

( x i ) SEQUENCE DESCRIPTION: SEQ ID NO:3:

```
Met Met Asp Gln Ala Arg Ser Ala Phe Ser Asn Leu Phe Gly Gly Glu
 1           5                    10                  15

Pro Leu Ser Tyr Thr Arg Phe Ser Leu Ala Arg Gln Val Asp Gly Asp
            20                  25                  30

Asn Ser His Val Glu Met Lys Leu Ala Ala Asp Glu Glu Glu Asn Ala
            35              40                  45

Asp Asn Asn Met Lys Ala Ser Val Arg Lys Pro Lys Arg
    50              55                  60
```

( 2 ) INFORMATION FOR SEQ ID NO:4:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Hamster ( i x ) FEATURE:
        ( A ) NAME/KEY: Protein
        ( B ) LOCATION: 1..61

( x i ) SEQUENCE DESCRIPTION: SEQ ID NO:4:

```
Met Met Asp Gln Ala Arg Ser Ala Phe Ser Asn Leu Phe Gly Gly Glu
 1           5                    10                  15

Pro Leu Ser Cys Thr Arg Phe Ser Leu Ala Arg Gln Val Asp Gly Asp
            20                  25                  30

Asn Ser His Val Glu Met Lys Leu Ala Val Asp Glu Glu Glu Asn Ala
            35              40                  45

Asp Asn Asn Thr Lys Ala Asn Val Thr Lys Pro Lys Arg
    50              55                  60
```

MONOCLONAL ANTIBODIES REACTIVE WITH TRANSFERRIN RECEPTOR CYTOPLASMIC DOMAIN

This invention was made with Government support under Grant No. CA 34787 awarded by the National Institutes of Health. The Government has certain rights in this invention.

This is a continuation of application Ser. No. 07/871,105, filed Apr. 20, 1992, now abandoned.

BACKGROUND OF THE INVENTION

1. Field of the Invention

The invention relates to monoclonal antibodies capable of binding to transferrin receptor (TR) cytoplasmic domain, hybridomas producing these antibodies, and methods of using these monoclonal antibodies to isolate endosomal TR cytoplasmic domain sequences.

2. Related Art

Receptor-mediated endocytosis is the mechanism by which a variety of nutrients, hormones, and growth factors are specifically and efficiently transported into the cell. The process of receptor mediated endocytosis is complex and involves several distinct biochemical steps. Typically, the process proceeds by: (1) recruitment of soluble coat proteins to the cell membrane and nucleation of coated pit formation; (2) assembly of coat constituents and growth of the coated pit; (3) acquisition of specific receptors into the growing coated pit; (4) invagination of the cell membrane, (5) coat closure; and (6) membrane fusion wherein the coated pit buds in and pinches off to form a coated vesicle. The contents of the vesicles are ultimately delivered to the endosomes. Key to the entire process of receptor-mediator endocytosis is the internalization signal present in the cytoplasmic tail of the receptor. The cytoplasmic tail interacts with soluble coat proteins during formation of a coated pit.

Receptors such as the transferrin receptor (TR) and the low-density lipoprotein (LDL) receptor are constitutively clustered in coated pits and undergo rapid internalization in both the presence and absence of ligand. Other receptors such as epidermal growth factor (EGF) receptor are only concentrated in coated pits and internalized after binding ligand. Previous studies have established that there are internalization signals in the cytoplasmic domains of constitutively recycling receptors that are believed to interact with adaptor proteins of coated pits and promote high-efficiency endocytosis.

Transferrin receptors (TR) bind the serum transport protein transferrin (Tf) and mediate uptake of iron into the cell. The TR is a homodimeric type II membrane protein consisting of two identical ~95 kD subunits covalently linked by two intermolecular disulfide bonds (Jing, et al., *EMBO J.*, 6:327–331, 1987). The primary structures of human, mouse, and chicken TRs have been deduced from sequencing of their respective cDNAs and are similar (Schneider, et al., *Nature*, 311:675–678, 1984; McClelland, et al., *Cell*, 39:267–274, 1984; Gerhardt, et al., *Gene*, 102: 249–254, 1991). The human TR has an extracellular domain of 671 amino acids, a single 28-residue transmembrane region and a 61 residue amino-terminal cytoplasmic domain. The TR is a member of the class of ligand transport receptors that are constitutively clustered in coated pits and are rapidly internalized (Goldstein, et al., *Ann. Rev. Cell. Biol.*, 1:1–39, 1985; Trowbridge, *Current Opinions in Cell Biology*, 3:633–642, 1991). A tetrapeptide sequence, YXRF, in the cytoplasmic tail of the TR has been identified as the recognition motif for high-efficiency endocytosis (Collawn, et al., *Cell*, 63:1061–1072, 1990).

MAbs have been obtained that react with the external domains of human, mouse, rat and chick TRs (Trowbridge, et al., *Proc. Natl. Acad. Sci. USA*, 78:3039–3043, 1981; Trowbridge, et al., *J. Cell. Physiol.*, 112:403–410, 1982; Jeffries, et al., *Immunology*, 54:333–341–1985; Schmidt, et al., *Biochem. J.*, 232:735–741, 1985) and have been useful in characterization of the receptor and studies of its function (Omary, et al., *J. Biol. Chem.*, 256:12888–12892, 1981; Schneider, et al., *J. Biol. Chem.*, 257:8516–8522, 1982; Hopkins, et al., *J. Cell Biol.*, 97:508–521, 1983). Some anti-TR external domain MAbs, either singularly or in combination, block Tf-mediated iron uptake and, as a consequence, inhibit cell growth (Trowbridge, et al., *Proc. Natl. Acad. Sci. USA*, 79:1175–1179, 1982; Lesley, et al., *Mol. Cell. Biol.*, 4:1675–1681, 1984; White, et al., *Cancer Res.*, 50:6295–6301, 1990). Such antibodies are potential therapeutic agents in the treatment of cancer (White, ibid; Trowbridge, *Progress in Allergy*, 45:121–146, 1988). However, although MAbs have been produced against the external domain of the TR, no MAbs to the TR cytoplasmic domain have been reported even though such MAbs would be useful in studying the mechanisms associated with vesicle formation and in providing a means for isolating and purifying endosomal vesicles. The present invention addresses this need and provides methods for isolating endosomes by means of antibodies provided by the invention.

BRIEF DESCRIPTION OF THE FIGURE

FIG. 1. Schematic diagram summarizing the localization of the epitopes detected by antihuman TR cytoplasmic tail MABs to specific regions of the human TR cytoplasmic domain. The complete amino acid sequence of the human cytoplasmic tail is shown and the positions at which there are amino acid substitutions in the mouse and Chinese hamster TR cytoplasmic tails are indicated.

SUMMARY OF THE INVENTION

The present invention provides monoclonal antibodies which bind to the transferrin receptor cytoplasmic domain and hybridomas which produce these monoclonal antibodies. Also provided are amino acid sequences which specifically bind to the paratope of these monoclonal antibodies and which can be used immunogenically to produce antibodies that specifically bind these peptides. The monoclonal antibodies of the invention find particular utility as reagents for detecting the presence of the transferrin receptor at various times during endosomal development and in purification of endosomes, thereby allowing determination of the contents of the invaginated endosomal vesicle. In addition, the antibodies of the invention can be expressed in a mammalian host cell for therapeutic purposes to thereby inhibit the internalization of transferrin receptors.

DETAILED DESCRIPTION OF THE INVENTION

The present invention relates to monoclonal antibodies which are specific for the cytoplasmic domain of the transferrin receptor (TR). In a preferred embodiment of the invention, monoclonal antibodies are disclosed which are capable of binding epitopic polypeptide sequences in the TR cytoplasmic domain. Also disclosed are polypeptides which are specifically bound by these antibodies. This specificity enables the monoclonal antibody, and like monoclonal antibodies with like specificity, to be used to bind the TR cytoplasmic domain in isolating compositions comprising the TR cytoplasmic domain, such as vesicles associated with receptor-mediated endocytosis.

The general method used for production of hybridomas producing monoclonal antibody is well known (Kohler and Milstein, *Nature*, 256:495, 1975). Briefly, BALB/c mice were immunized with purified recombinant human TR and hybridomas were produced using standard techniques. The resulting hybridomas were then screened for production of monoclonal antibodies capable of binding to human TR.

In one aspect, the present invention is directed to monoclonal antibodies which are reactive with the TR cytoplasmic domain and hybridomas which produce such antibodies. The isolation of hybridomas producing monoclonal antibodies of the invention can be accomplished using routine screening techniques which permit determination of the elementary reaction pattern of the monoclonal antibody of interest. Thus, if a monoclonal antibody being tested binds with the TR cytoplasmic domain, then the antibody being tested and the antibody produced by the hybridomas of the invention are equivalent.

Alternatively, since the invention teaches the polypeptide or amino acid sequences in the TR cytoplasmic domain which are specifically required for binding of the preferred monoclonal antibodies of the invention, it is now possible to use these peptides for purposes of immunization to produce hybridomas which produce monoclonal antibodies specific for the TR cytoplasmic domain. This approach has the added advantage of decreasing the repertoire of monoclonal antibodies generated by limiting the number of antigenic determinants presented at immunization. The monoclonal antibodies produced by this method can be screened for specificity using standard techniques, for example, by binding polypeptide sequence or TR cytoplasmic domain to a microtiter plate and measuring binding of the monoclonal antibody by an ELISA assay.

It is also possible to determine, without undue experimentation, if a monoclonal antibody has the same specificity as a monoclonal antibody of the invention by ascertaining whether the former prevents the latter from binding the TR cytoplasmic domain. If the monoclonal antibody being tested competes with the monoclonal antibody of the invention, as shown by a decrease in binding by the monoclonal antibody of the invention, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the TR cytoplasmic domain with which it is normally reactive, and then add the monoclonal antibody being tested to determine if the monoclonal antibody being tested is inhibited in its ability to bind the antigen. If the monoclonal antibody being tested is inhibited then, in all likelihood, it has the same, or a closely related, epitopic specificity as the monoclonal antibody of the invention.

Screening of monoclonal antibodies of the invention, can be carried out utilizing polypeptides having an appropriate sequence, i.e., LARQ for monoclonal antibodies with the specificity of H68.4, and VDGDNSH for monoclonal antibodies with the specificity of H73.2.

Under certain circumstances, monoclonal antibodies of one isotype might be more preferable than those of another. Particular isotypes of a monoclonal antibody can be prepared either directly, by selecting from the initial fusion, or prepared secondarily, from a parental hybridoma secreting a monoclonal antibody of different isotype by using the sib selection technique to isolate class-switch variants (Steplewski, et al., *Proceedings of the National Academy of Science*, U.S.A., 82:8653, 1985; Spira, et al., *Journal of Immunological Methods*, 74:307, 1984). Thus, the monoclonal antibodies of the invention would include class-switch variants having specificity for an epitope in the TR cytoplasmic domain.

The isolation of other hybridomas secreting monoclonal antibodies with the specificity of the monoclonal antibodies of the invention can also be accomplished by one of ordinary skill in the art by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibody produced by a single hybridoma which was used to immunize the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody could be used for immunization since the anti-idiotype monoclonal antibody binding domain effectively acts as an antigen.

The term "antibody" as used in this invention is meant to include intact molecules as well as fragments thereof, such as Fab and F(ab')$_2$, which are capable of binding the epitopic determinant.

The monoclonal antibodies of the invention can be bound to many different carriers and used to detect the presence of TR cytoplasmic domain. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As used in this invention, the term "epitope" any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

A preferred embodiment of the invention comprises the epitopic polypeptides LARQ, VDGDNSH, and conservative variations of these peptides. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Peptides of the invention can be synthesized by the well known solid phase peptide synthesis methods described by Merrifield, *J. Am. Chem. Soc.* 85:2149, 1962, and Stewart and Young, *Solid Phase Peptides Synthesis*, (Freeman, San Francisco, 1969, pp. 27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid-phase Edman degradation.

During or after the synthesis, reactive amino acids may be protected by various blocking groups, for example, cysteines may be blocked by 3,4-dimethylbenzyl (DMB) groups, arginines and histidines by tosyl (TOS) groups, aspartic acid and glutamic acids by benzyl (Bzl) groups, and lysines the 2-chlorobenzyloxycarboxyl (2-CBZ) groups. Other protective blocking groups are well-known, and can be used in the present invention. Those of ordinary skill in the art will know of other techniques for peptide synthesis, or can readily ascertain such techniques, without resorting to undue experimentation.

The techniques of sensitization and/or immunization, cell fusion, ascites production, selection of mixed hybridomas, or subcloning of monoclonal hybridomas are generally well known in the art. Attention is directed to Koprowski, et al., U.S. Pat. No. 4,172,124, Koprowski, et al., U.S. Pat. No. 4,196,265, or Douillard, J. Y. and Hoffman, T., *Basic Facts about Hybridomas*, in *Compendium of Immunology*, Vol. II, L. Schwartz, ed. (1981), which are herein incorporated by reference.

In general, the purified epitopic peptides containing TR cytoplasmic domain specific sequences have a cystine attached at the C-terminus to permit unidirectional attachment of the synthetic peptide to an immunogenic protein through a connecting bridge, e.g., maleimidobenzoylated (MB)-keyhole limpet hemocyanin (KLH). Other immunogenic conjugates can also be used, e.g., albumin, and the like. The resulting structure may have several peptide structures linked to one molecule of protein.

Somatic cells derived from a host immunized against the synthetic peptides can be obtained by any suitable immunization technique. The host subject is immunized by administering the antigen, usually in the form of a protein conjugate, as indicated above, by any suitable method, preferably by injection, either intraperitoneally, intravenously, subcutaneously, or by intra-foot pad. Adjuvants may be included in the immunization protocol.

The initial immunization with the protein bound antigen can be followed by several booster injections given periodically at intervals of several weeks. The antibody contained in the plasma of each host can then be tested for its reactivity with TR cytoplasmic domain or peptide fragment. The host having the highest response is usually most desirable as the donor of the antibody secreting somatic cells used in the production of hybridomas. Alternatively, hyperimmunization can be effected by repeatedly injecting additional amounts of peptide-protein conjugate by intravenous and/or intraperitoneal route.

The monoclonal antibodies of the invention can be used in immunoaffinity chromatography for the isolation of sequences containing TR cytoplasmic domain mentioned herein. One way by which such immunoaffinity chromatography can be utilized is through the use of, for example, the binding of the monoclonal antibodies of the invention to CNBr-Sepharose-4B or Tresyl-activated Sepharose (Pharmacia). These solid phase-bound monoclonal antibodies can then be used to specifically bind sequences containing TR cytoplasmic domain from mixtures of other proteins to enable isolation and purification thereof. Bound TR cytoplasmic domain sequences can be eluted from the affinity chromatographic material using techniques known to those of ordinary skill in the art such as, for example, chaotropic agents, low pH, or urea. This technique is particularly useful for isolating endosomal vesicles from a lysed cellular preparation and thereby allow analysis of the endosomal contents, for example.

The invention now being fully described, it will be apparent to one of ordinary skill in the art that various changes and modifications can be made without departing from the spirit or scope of the invention.

EXAMPLE 1

PREPARATION OF HYBRIDOMA CELL LINES PRODUCING MONOCLONAL ANTIBODIES TO TRANSFERRIN RECEPTOR CYTOPLASMIC REGION

Recombinant human TR for immunization was produced in a baculovirus expression system (Domingo, et al., *J. Biol.*

Chem., 263:13386–13392, 1988) and purified on a human transferrin (Tf) affinity column (White, ibid; Domingo, ibid). Anti-TR MAbs were obtained by immunization of BALB/c mice with purified receptor glycoprotein and hybridomas (White, ibid) prepared using protocols previously described. Hybridomas producing anti-TR MAbs were identified by an ELISA assay for reactivity to recombinant human TR and cloned by limiting dilution (White, ibid). These fusions produced 35 stable, cloned hybridomas secreting MAbs against human TR that were detected by ELISA. Isotyping of MAbs was performed using an ELISA isotyping kit according to the manufacturer's instructions (Mono Ab-ID IEA Kit; Zymed Laboratories, Inc., San Francisco, Calif.). H68.4 and I60.1 were typed as IgG1 MAbs and H73.2 as an IgG3 MAb.

Monoclonal antibodies produced by the various hybridomas were screened for reactivity with cell cultures and cell culture extracts. In these studies, C/E CEF (chicken embryo fibroblast) cells were obtained from SPAFAS (Specific Pathogen Free Avian Supplies) (Norwich, Conn.) and grown in Dulbecco's modified Eagle's medium (DMEM) supplemented with 1% (v/v) chicken serum, 1% (v/v) defined calf bovine serum (High Clone, Logan, Utah), 2% (v/v) tryptose broth (Difco, Detroit, Mich.) (Jing, et al., J. Cell Biol., 110:283–294, 1990). Chinese hamster ovary (CHO) cells and mouse L cells were cultured in DMEM supplemented with 8% defined calf bovine serum. Human T leukemic cells, CCRF-CEM (White, ibid.), were cultured in RPMI 1640 medium supplemented with 8% defined calf bovine serum.

In utilizing flow cytofluorimetric analysis to determine the binding of anti-human TR MAbs to CCRF-CEM cells, $2 \times 10^6$ CCRF-CEM cells were stained at 4° C. with 100 µl of hybridoma tissue culture supernatant followed by saturating amounts of fluoresceinated goat-anti-mouse immunoglobulin as second antibody (White, ibid). MAb B3/25 was used as a positive control for TR binding; the negative control was tissue culture medium without MAb. When examined by flow cytometry, 32 of the MAbs were found to be specific for the external domain of the TR receptor as shown by their binding to the surface of viable CCRF-CEM cells. The remaining monoclonal antibodies (H68.4, H73.2, I60.1) did not bind to the surface of intact CCRF-CEM cells.

Monoclonal antibodies produced as described above were also analyzed by immunoprecipitation. In these studies, cell surface iodination, immunoprecipitation, and SDS-polyacrylamide gel electrophoresis were performed as described previously, except that CEF were surface-iodinated as monolayers (Domingo, ibid). Briefly, confluent CEF cultures in 10 cm tissue culture dishes were iodinated with 1 mCi Na$^{125}$I (Amersham, Arlington Heights, Ill.), in 2.5 ml of 0.15M NaCl-0.01M Na phosphate buffer (pH 7.2 PBS) by the lactoperoxidase-glucose oxidase technique (Trowbridge, et al., Proc. Natl. Acad. Sci. USA, 72:157–161, 1975). Cells were lysed in 1 ml of 1% Nonidet P-40 in PBS and 50–100 µl of cell lysate used for immunoprecipitation with 50 µl of hybridoma tissue culture supernatant. Antibody-antigen complexes were then adsorbed to fixed S. aureus precoated with rabbit anti-mouse immunoglobulin as described (Domingo, ibid). Samples were subjected to electrophoresis on 7.5% SDS-polyacrylamide gels under reducing conditions.

Mutant human TRs were expressed in CEF using the helper-independent retroviral vector, BH-RCAS, as described previously (Jing, ibid). The construction, expression, and properties of all the mutant human TRs used in the present study are described in Collawn, et al. (Cell, 61:1061, 1990) and Jing, et al. (J. Cell Biol., 110:283, 1990).

In these studies, MAbs were compared with respect to their ability to immunoprecipitate wildtype human TRs or "tailless" (Δ3-59) mutant human TRs lacking residues 3–59 of the amino-terminal cytoplasmic domain (Jing, ibid). B3/25 MAb, an antibody against the external domain of the human TR (Trowbridge, et al., Proc. Natl. Acad. Sci USA, 78:3039–3043, 1981; Omary, et al., J. Biol. Chem., 256:12888–12892, 1981), immunoprecipitated both the wildtype and "tailless" receptors from detergent lysates of surface-iodinated CEF expressing recombinant human TRs. In contrast, MAbs H68.4, H73.2, and I60.1 immunoprecipitated wildtype TRs, but not the "tailless" mutant receptors, clearly establishing that these latter monoclonal antibodies were directed against epitopes located in the cytoplasmic tail of the human TR.

EXAMPLE 2

CHARACTERIZATION OF MONOCLONAL ANTIBODIES SPECIFIC FOR TRANSFERRIN RECEPTOR CYTOPLASMIC DOMAIN

The epitope recognized by the cytoplasmic tail specific MAbs were localized by comparing binding to wildtype and mutant human TRs. Mutant human TRs with either deletions or single amino acid substitutions in their cytoplasmic domains (Collawn, ibid.; Jing, ibid.) were used to define the epitopes recognized by each of the MAbs. Immunoprecipitation studies with two deletion mutants, Δ3-28 and Δ3-35 established that each MAb recognized a different epitope. In contrast to the other two MAbs, H68.4 MAb did not react with the Δ3-28 mutant TR, localizing its epitope to residues 3-28 of the human TR tail.

Although H73.2 MAb immunoprecipitated the Δ3-28 mutant TR, albeit less efficiently than wildtype receptors, this MAb did not react with the Δ3-35 mutant TR. The differential reactivity of H73.2 MAb with the Δ3-28 and Δ3-35 mutant TRs maps the epitope recognized by this MAb quite precisely to residues 29–35.

Since Mab I60.1 reacted with both deletion mutants, the epitope recognized by thin monoclonal antibody is also distinct and is located between residues 36 and 61. As the YXRF tetrapeptide internalization signal of the human TR encompasses residues 20–23 of the cytoplasmic tail, it was possible that the MAb H68.4 might bind directly to the receptor internalization signal. However, immunoprecipitation studies with mutant human TRs with each residue of the internalization signal independently altered to alanine demonstrated that the epitope recognized by MAb H68.4 was distinct from the internalization signal. MAb H68.4 did not react with a mutant human TR, however, in which Ala-26 had been altered to Phe, suggesting that its epitope was located proximal to the carboxy-terminal side of the TR internalization signal.

The reactivity of MAb H73.2 was also reduced by altering Ala-25 to Phe, raising the possibility that this single amino acid substitution might induce an extensive conformational change in the amino-terminal region of the human TR cytoplasmic tail. Consequently, immunoprecipitation studies were also performed with a mutant human TR (Δ25-28) lacking residues 25–28, previously shown to retain internalization activity (Collawn, et al., Cell, 63:1061–1072, 1990). Deletion of these four residues abolished reactivity with MAb H68.4 without affecting that of MAb H73.2. Consequently, the epitope recognized by MAb H68.4 is proximal to the carboxy-terminal side of the internalization recognition signal and includes residues 25–28 of the human TR cytoplasmic tail.

The primary structure of the TR cytoplasmic tail is highly conserved in the three mammalian species for which cDNA nucleotide sequences encoding their cytoplasmic tails have been determined (Schneider, et al., *Nature*, 311:675, 1984; McClelland, et al., *Cell*, 39:267, 1984; Gerhardt, et al., *Gene*, 102:249, 1991; Alvarez, et al., *Biochem. J.*, 267:31–35, 1990). Strikingly, the deduced amino acid sequences of mouse and Chinese hamster TRs are identical to that of the human TR in the region of the cytoplasmic tail where the epitope maps for H68.4 and H73.2 are located, implying that both MAbs should crossreact with mouse and Chinese hamster TRs. To test this prediction, immunoprecipitation studies were performed using mouse L cells and CHO cells. Consistent with the results of epitope mapping, both H68.4 and H73.2 MAbs reacted with mouse and Chinese hamster TRs. In contrast, the third anti-TR cytoplasmic tail MAb, I60.1, immunoprecipitated the Chinese hamster TR, but not the mouse TR. As all but one of the amino acid differences between the cytoplasmic tail of mouse TR and those of human and Chinese hamster TRs are found in the membrane-proximal of the cytoplasmic tail between residues 52–61 (FIG. 1 ), it is likely that the epitope recognized by MAb I60.1 is localized to this 10 residue carboxy-terminal region of the cytoplasmic tail.

Studies were also done on the membrane labelling characteristics of the monoclonal antibodies. Anti-human TR MAbs, B3/25 and H68.4, were complexed to colloidal gold and used to decorate CEF plasma membranes prepared by a surface replica technique (Miller, et al., *Cell*, 65:621–632, 1991). Cells were incubated with 6 nm B3/25 gold complexes and then the upper plasma membrane removed onto a coverslip exactly as described previously. The stripped membranes were then fixed in 2% paraformaldehyde, quenched and incubated with H68.4 3 nm gold complexes as if they were cryosections (Miller, et al., *J. Cell Biol.*, 102, 1986). Control sections were pre-incubated with free antibody; nonspecific labeling under these conditions was negligible. Finally, still adherent to the coverslip, the stripped membranes were critical point dried, rotary shadowed and whole mounts prepared for electron microscopy (Miller, ibid).

In previous studies using B3/25 gold complexes, it was demonstrated that, at expression levels in the range $2\times10^5$ to $8\times10^5$, 6% of the human TR were located in clathrin-coated domains. Some of these lattices covered invaginating membrane and were typical coated pits while others were flat lattices, unrelated to invaginated membrane. In the present experiments, conjugates of the anti-TR cytoplasmic tail MAb H68.4 did not label lattice coated areas. To investigate this question further, quantitative, double label experiments were carried out in which the external domain of the wildtype human TR's were labelled with B3/25 6 nm gold complexes and the cytoplasmic tails subsequently labelled with H68.4 complexed to 3 nm gold. In these studies, the 6 nm complexes were seen through the full thickness of the plasma membrane and were frequently distributed within lattice coated areas. However, outside these areas, the majority of H68.4 gold particles (86%) were distributed within 25 nm of B3/25 6 nm gold complexes. This data shows that gold complexes can label aggregates of human TR from both sides of the membrane, but that when these receptors become. incorporated into a lattice, their cytoplasmic domains are no longer accessible to the H68.4/gold complex.

The results presented herein clearly establish that MAbs H68.4, H73.2 and I60.1 are directed against the human TR cytoplasmic tail. Although MAbs have been obtained against the external domain of the human TR (Trowbridge, ibid.; White, ibid.; Sutherland, et al., *Proc. Natl. Acad. Sci. USA*, 78:4515–4519, 1981), none against the cytoplasmic domain of the receptor have previously been reported. One reason that MAbs against the cytoplasmic domain of human TR have been difficult to generate is that the primary structures of the cytoplasmic tails of mammalian TRs are highly conserved with four amino acid differences between mouse and human (Gerhardt, ibid.; Rothenberger, et al., *Cell*, 49:423–431, 1987), and apparently only one between Chinese hamster and human (Alvarez, ibid). In contrast, the much larger external domains of human and mouse TRs are only 77% identical (Gerhardt, ibid).

Two of the three MAbs, H68.4 and H73.2, react with epitopes in a region of the human TR cytoplasmic tail that is completely conserved in mouse and Chinese hamster and, therefore, it is not surprising that the MAbs recognize TRs from these species. All three MAbs also crossreact with Chinese hamster TR, and given the highly conserved nature of the amino-terminal region of the TR cytoplasmic domain, it is likely that many mammalian TRs will be recognized by one or more of these anti-human TR cytoplasmic tail MAbs. The broad species cross-reactivity of the MAbs against the TR cytoplasmic tail contrasts to the relatively high species-specificity of MAbs against the external domain of the human TR. The fact that apparently high-affinity autoantibodies can be generated against the TR cytoplasmic tail indicates that its intracellular location on the cytoplasmic face of the cell membrane is an immunologically privileged site from which it is not released in an antigenic form. From a panel of 32 murine MAbs against external epitopes of the human TR, only 6 crossreacted with baboon or macaque TRs.

An interesting feature of MAb H68.4 is its selective reactivity with TRs outside clathrin-coated pits when the cytoplasmic face of plasma membrane preparations are stained with antibody-gold complexes. The MAb H68.4 epitope maps close to the TR internalization signal, which is thought to bind to plasma membrane coated pit adaptor complexes (Pearse, *EMBO J.*, 7:3331–3336, 1988; Glickman, et al., *EMBO J.*, 8:1041–1047, 1989; Pearse, et al., *Ann. Rev. Cell. Biol.*, 6:151–171, 1990). A likely explanation for the selective reactivity of H68.4 is, therefore, that its binding is sterically blocked by adaptor proteins associated with the cytoplasmic tails of receptors in clathrin-coated pits. This interpretation is consistent with the ability of MAb H68.4 to inhibit internalization of TRs (Schmid, et al., *J. Cell Biol.*, 114:869–880, 1991), as would be expected if the MAb could reciprocally block binding of adaptor proteins to the TR cytoplasmic tail.

Deposit of Materials

The following cell lines have been deposited before Apr. 20, 1992, with the American Type Culture Collection, 1301 Parklawn Drive, Rockville, Md., U.S.A. (ATCC):

| Cell Line | ATCC Accession No. | DATE |
| --- | --- | --- |
| H 68.4 | HB 11011 | April 7, 1992 |
| H 73.2 | HB 11010 | April 7, 1992 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

We claim:

1. A hybridoma which produces monoclonal antibodies which bind specifically to the transferrin receptor cytoplasmic domain, wherein the hybridoma has an accession number selected from the group consisting of ATCC HB 11011 and HB 11010.

2. A monoclonal antibody produced by ATCC HB 11011.

3. A monoclonal antibody produced by ATCC HB 11010.

4. A method of producing a monoclonal antibody of claim 2 comprising immunizing an animal with a human transferrin receptor polypeptide or a peptide having an amino acid sequence of LARQ conjugated to an immunogenic protein, preparing a hybridoma cell line ATCC HB 11011 and obtaining antibodies produced by said hybridoma cell line.

5. A method of producing a monoclonal antibody of claim 3 comprising immunizing an animal with a human transferrin receptor polypeptide or a peptide having an amino acid sequence of VDGDNSH conjugated to an immunogenic protein, preparing a hybridoma cell line ATCC HB 11010 and obtaining antibodies produced by said hybridoma cell line.

\* \* \* \* \*